United States Patent [19]

Sestanj

[11] 4,369,188
[45] Jan. 18, 1983

[54] 2-THIOXOBENZ[CD]INDOLE-1(2H)-ACETIC ACID DERIVATIVES

[75] Inventor: Kazimir Sestanj, St. Laurent, Canada

[73] Assignee: Ayerst, McKenna & Harrison Inc., Montreal, Canada

[21] Appl. No.: 284,049

[22] Filed: Jul. 17, 1981

[51] Int. Cl.³ .................. C07D 209/90; A61K 31/40
[52] U.S. Cl. ..................................... 424/274; 548/437
[58] Field of Search ................... 260/326.27; 424/274

[56] References Cited

U.S. PATENT DOCUMENTS

| 3,386,986 | 6/1968 | Brach | 260/326.27 |
| 3,755,353 | 8/1973 | Baumann et al. | 260/236.27 |
| 3,821,383 | 6/1974 | Sestanj et al. | 424/258 |
| 3,853,911 | 12/1974 | Scnefczik | 260/326.27 |
| 4,080,331 | 3/1978 | Brack | 260/326.27 |
| 4,254,108 | 3/1981 | Sestanj | 424/258 |
| 4,254,109 | 3/1981 | Sestanj | 424/258 |

FOREIGN PATENT DOCUMENTS

| 2429760 | 1/1976 | Fed. Rep. of Germany | 260/326.27 |
| 55-142056 | 11/1980 | Japan | 260/326.27 |
| 183756 | 7/1966 | U.S.S.R. | 260/326.27 |
| 445646 | 10/1974 | U.S.S.R. | 260/326.27 |

OTHER PUBLICATIONS

Karishin et al.; Chem. Abs., vol. 88:21753e (1978).
Rozhinskii et al.; Chem. Abs., vol. 78:29537b (1973).
Vul'fson et al.; Chem. Abs., vol. 71:82627n (1968).
Karishin et al.; Chem. Abs., vol. 89:163333n (1978).
Dutt; J. Chem. Soc., 224 (1923).
Dvornik et al.; Science, vol. 182, p. 1146 (1973).
Pechka et al.; Chem. Abs., vol. 87:184310b (1977).

Primary Examiner—Mary C. Lee
Attorney, Agent, or Firm—Arthur E. Wilfond

[57] ABSTRACT

Herein are disclosed compounds of the formula

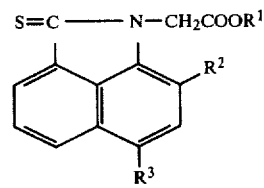

in which $R^1$ is hydrogen, lower alkyl or $-(CH_2)_m-NR^4R^5$ wherein m is an integer from 2 to 6 and $R^4$ and $R^5$ each is hydrogen or lower alkyl; $R^2$ is hydrogen, bromo or chloro; and $R^3$ is hydrogen or halo; with the requirement that when $R^2$ is bromo or chloro, then $R^3$ is bromo or chloro or a therapeutically acceptable salt thereof. The compounds inhibit lens aldose reductase in a diabetic mammal.

17 Claims, No Drawings

2-THIOXOBENZ[CD]INDOLE-1(2H)-ACETIC ACID DERIVATIVES

BACKGROUND OF THE INVENTION

This invention relates to 2-thioxobenz[cd]indole-1(2H)-acetic acid derivatives, therapeutically acceptable salts thereof, a process for their preparation and to pharmaceutical compositions thereof. The derivatives are potent inhibitors of lens aldose reductase which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, atherosclerosis and cataracts. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

A number of benz[cd]indoles are described and exemplified in the following reports: Chemical Abstracts, 88, 21753e (1978) citing Zh. Obshch. Khim., 47, 2042 (1977); Chemical Abstracts, 84, 107080n (1976) citing Ger. Offen., 2,429,760, Jan. 15, 1976; Chemical Abstracts, 66, 46327c (1967) citing U.S.S.R. Pat. No. 183,756, July 9, 1966; Chemical Abstracts, 82, 97936p (1975) citing U.S.S.R. Pat. No. 445,646, Oct. 5, 1974; Chemical Abstracts, 78, 29537b (1973) citing Zh. Org. Khim., 8, 2177-81 (1972); A. Brach, U.S. Pat. No. 3,386,986, June 4, 1968; Chemical Abstracts, 71, 82627n (1969) citing Ivz. Akad. Nauk. SSSR, Ser. Khim., (6), 1390-2 (1969); Chemical Abstracts, 89, 163333n (1978) citing Zh. Org. Khim., 14, 1095-7 (1978); and S. Dutt, J. Chem. Soc., 224 (1923). The compounds of the above reports are distinguished from the compounds of this application by having different chemical structures, and by not being indicated for use as inhibitors of lens aldose reductase.

Another different chemical ring system, 1,3-dioxo-1H-benz[de]isoquinoline-2(3H)-acetic acid and derivatives thereof are reported to be inhibitors of lens aldose reductase by D. Dvornik et al., Science, 182, 1146 (1973) and K. Sestanj et al., U.S. Pat. No. 3,821,383, June 27, 1974; K. Sestanj, U.S. Pat. No. 4,254,108, Mar. 3, 1981; and K. Sestanj, U.S. Pat. No. 4,254,109, Mar. 3, 1981.

SUMMARY OF THE INVENTION

The compounds of this invention are represented by formula I

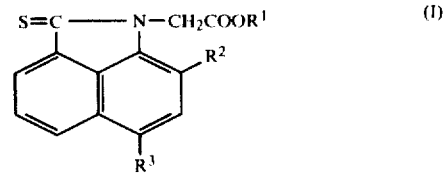

in which $R^1$ is hydrogen, lower alkyl, or $-(CH_2)_m-NR^4R^5$ wherein m is an integer from 2 to 6 and $R^4$ and $R^5$ each is hydrogen or lower alkyl; $R^2$ is hydrogen, bromo, or chloro; and $R^3$ is hydrogen or halo; with the requirement that when $R^2$ is bromo or chloro, then $R^3$ is bromo or chloro, or a therapeutically acceptable salt thereof.

Preferred compounds of formula I are those in which $R^1$ is hydrogen, lower alkyl, or $-(CH_2)_m-NR^4R^5$ wherein m is 2 or 3 and $R^4$ and $R^5$ each is hydrogen, methyl or ethyl; $R^2$ is hydrogen and $R^3$ is hydrogen or halo; or $R^2$ and $R^3$ are the same and are selected from bromo or chloro; or a therapeutically acceptable salt thereof.

Another preferred group of compounds of this invention is represented by formula I in which $R^1$ and $R^2$ are hydrogen, and $R^3$ is hydrogen or halo; or in which $R^1$ is hydrogen and $R^2$ and $R^3$ are the same and are selected from bromo or chloro; or a therapeutically acceptable base addition salt thereof.

The compounds of formula I are prepared by reacting a compound of formula II

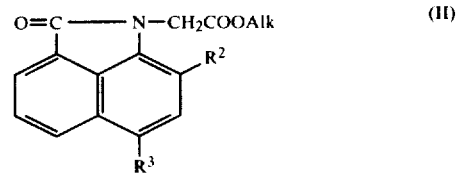

in which Alk is lower alkyl and $R^2$ and $R^3$ are as defined herein, with phosphorus pentasulfide to obtain the corresponding compound of formula I in which $R^1$ is lower alkyl, and $R^2$ and $R^3$ are as defined herein; and if desired, converting the compound of formula I in which $R^1$ is lower alkyl to another compound of formula I in which $R^1$ is hydrogen, or $-(CH_2)_m-NR^4R^5$ wherein m, $R^4$ and $R^5$ are as defined herein, and $R^2$ and $R^3$ are as defined herein.

A method is provided for preventing or relieving diabetes mellitus associated complications in a diabetic mammal by administering to said mammal an alleviating or prophylactic amount of the compound of formula I or a therapeutically acceptable salt thereof. Preferred complications are selected from cataracts, neuropathy, nephropathy or retinopathy.

Compounds of formula I, or a therapeutically acceptable salt thereof, when admixed with a pharmaceutically acceptable carrier, form a pharmaceutical composition which can be used according to the preceding method.

DETAILED DESCRIPTION OF THE INVENTION

The term "lower alkyl" as used herein means straight chain alkyl radicals containing from one to six carbon atoms, preferably one to three carbon atoms, and branched chain alkyl radicals containing three or four carbon atoms and includes methyl, ethyl, propyl, 1-methylethyl, butyl, 1,1-dimethylethyl, pentyl, hexyl and the like.

The term "halo" as used herein means halo radicals and includes fluoro, chloro, bromo and iodo, unless stated otherwise.

The term "lower alkanol" as used herein means straight and branched chain alkanols containing from one to four carbon atoms and includes methanol, ethanol, 1-methylethanol, butanol and the like.

The compounds of formula I, in which $R^1$ is hydrogen, form salts with therapeutically acceptable inorganic and organic bases. These derived salts possess the same activity as the parent acid and are included within the scope of this invention. The acid is transformed in excellent yield into the corresponding therapeutically acceptable salt by neutralization of the acid with the appropriate inorganic or organic base. The salts are administered in the same manner as the parent acid compounds. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxylalkyl derivatives, such as N-methyl-morpholine and N-(2-hydroxyethyl)-piperidine; as well as pyridine. Furthermore, there may be mentioned the corresponding quaternary ammonium salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The amino compounds of formula I in which $R^1$ is $-(CH_2)_m-NR^4R^5$ are capable of forming acid addition salts with therapeutically acceptable acids. The acid additon salts are prepared by reacting the base form of the appropriate amino compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric, phosphoric acid, or the like; the organic acids, e.g. maleic, citric, tartaric acid, 4-methylphenyl sulfonic acid or the like; and acids which are sparingly soluble in body fluids and which impart slow-release properties to their respective salts, e.g. pamoic acid, tannic acid, carboxymethyl cellulose, or the like. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

A compound of formula I or an addition salt thereof can be administered to mammals, for example, man, cattle or rabbits, either alone or in dosage forms, i.e., capsules or tablets, combined with pharmacologically acceptable excipients, see below. Advantageously the compound can be given orally. However, the method of administering the compound is not to be construed as limited to a particular mode of administration. For example, the compound can be administered topically directly to the eye in the form of drops of sterile, buffered ophthalmic solutions, preferably of pH 7.2–7.6. Topical administration is especially useful for treating cataracts and retinopathy in a diabetic mammal. Also, it can be administered orally alone or in solid form containing such excipients as starch, milk sugar, certain types of clay and so forth. It can also be administered orally in the form of a solution or syrup, or it can be injected parenterally. For parenteral administration it can be used in the form of a sterile solution, preferably of pH 7.2–7.6 containing a pharmaceutically acceptable buffer. Oral and parenteral administration are the preferred routes for treating neuropathy and nephropathy in a diabetic mammal.

The dosage of the present therapeutic agent can vary with the form of administration. Furthermore, it can vary with the particular host under treatment. Generally, treatment is initiated with small dosages substantially less than the optimal dose of the compound. Thereafter, the dosage is increased by small increments until the optimal effect under the circumstances is reached. In general, the compound of formula I or an addition salt thereof is most desirably administered at a concentration level that will generally afford effective results without causing any harmful or deleterious side effects. For topical administration, a 0.05 to 0.2% solution can be administered dropwise to the eye. The frequency of instillation varies with the subject under treatment from a drop every two or three days to once daily. For oral or parenteral administration a preferred level of dosage ranges from about 1.0 mg to about 200 mg per kilogram of body weight per day, although aforementioned variations will occur. However, a dosage level that is in the range of from about 5.0 mg to about 200 mg per kilogram of body weight per day is most satisfactory.

Unit dosage forms such as capsules, tablets, pills and the like can contain from about 5 mg to about 500 mg of the compound of formula I or an addition salt thereof, dependent on the type of unit dosage, preferably with a significant quantity of pharmaceutical carrier. Thus, for oral administration, capsules can contain from between about 5 mg to about 500 mg of the compound of formula I or an addition salt thereof with or without a pharmaceutical diluent. Tablets, either effervescent or noneffervescent, can contain between about 5 to 500 mg of the compound of formula I or an addition salt thereof together with conventional pharmaceutical carriers. Thus, tablets which can be coated and either effervescent or noneffervescent can be prepared according to the known art. Inert diluents or carriers, for example, magnesium carbonate or lactose, can be used together with conventional disintegrating agents, for example, maize starch and alginic acid and lubricating agents for example, magnesium stearate.

Syrups or elixirs suitable for oral administration can be prepared from water soluble salts and can contain glycerol and ethyl alcohol as solvents or preservatives.

A compound of formula I or a therapeutically acceptable salt thereof also can be used in combination with insulin or oral hypoglycemic agents to produce beneficial effect in the treatment of diabetes mellitus. In this instance, commercially available insulin preparations or oral hypolycemic agents, exemplified by acetohexamide, chlorpropamide, tolazamide, tolbutamide and phenformin, are suitable. A compound of formula I or a therapeutically acceptable salt thereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S.A., 1980, "AMA Drug Evaluations", 3rd ed., PSG Publishing Co., Inc., Littleton, Mass., U.S.A., 1977, pp. 582–598, and "The Pharmacological Basis of Therapeutics", L. S. Goodman and A. Gilman, Eds., 5th ed., Macmillan Publishing Co., Inc., New York, N.Y., U.S.A., 1975, pp. 1507–1533. When used in combination, a compound of formula I or its therapeutically acceptable salt is administered as described previously. A compound of formula I or its therapeutically acceptable salt can be administered with the oral hypoglycemic agent in the form of a pharmaceutical composition comprising effective amounts of each agent.

The aldose reductase inhibiting effects of the compound of formula I or a therapeutically acceptable addition salt thereof can be demonstrated by employing an in vitro testing procedure similar to that described by S. Hayman and J. H. Kinoshita, J. Biol. Chem., 240, 877 (1965). In the present case, the procedure of Hayman and Kinoshita is modified in that the final chromatography step is omitted in the preparation of the enzyme from bovine lens.

Table 1 gives the results of the compounds of formula I or an addition salt thereof when evaluated in the above in vitro test.

TABLE 1

| Test Compound | % Inhibition at Different Molar Concentrations (in vitro) | | |
|---|---|---|---|
| | $10^{-5}$ | $10^{-6}$ | $10^{-7}$ |
| 2-thioxo-benz[cd]indole-1(2H)-acetic acid, ethyl ester | 66 | 11 | |
| 2-thioxo-benz[cd]indole-1(2H)-acetic acid | 93 | 87 | 61 |
| 6-bromo-2-thioxo-benz[cd]indole-1(2H)-acetic acid | 95 | 91 | 79 |
| 6-chloro-2-thioxo-benz[cd]indole-1(2H)-acetic acid | 96 | 91 | 66 |
| 6-fluoro-2-thioxo-benz[cd]indole-1(2H)-acetic acid | 94 | 88 | 56 |
| 6-iodo-2-thioxo-benz[cd]indole-1(2H)-acetic acid | 93 | 91 | 81 |
| 6,8-dibromo-2-thioxo-benz[cd]indole-1(2H)-acetic acid | 89 | 56 | 13 |
| 6,8-dichloro-2-thioxo-benz[cd]indole-1(2H)-acetic acid | 94 | 76 | 30 |
| 2-thioxo-benz[cd]indole-1(2H)-acetic acid, 2-amino-ethyl ester, 4-methylphenylsulfonic acid salt | 83 | 29 | |
| 6-chloro-benz[cd]indole-1(2H)-acetic acid, 3-dimethyl-amino-1-propyl ester, hydrochloride | 91 | 70 | 14 |

The aldose reductase inhibiting property of a compound of formula I and its utilization in diminishing and alleviating diabetic complications also are demonstrable in experiments using galactosemic rats, see D. Dvornik et al., Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent laboratory chow, Purina) and glucose at 20% (w/w %) concentration. The untreated galactosemic group was fed a similar diet in which galactose is substituted for glucose. The other groups were fed diets containing various amounts of the compound of formula I in the galacetose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and kept up to two weeks before being analyzed for dulcitol.

(c) The tissues were homoginized in 5% (w/v) trichloroacetic acid and the polyol determination on the extracts were performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissued from rats fed the glucose diet was subtracted from the individual values found in the corresponding rat tissue to obtain the amount of polyol accumulated].

The following experiments show that the compounds of formula I diminish and alleviate the accumulation of dulcitol in the lenses and sciatic nerves of rats fed galactose as compared to an untreated animal. The results obtained are exemplified in Table 2, wherein the values under L and N respectively, represent the percentage decreases of dulcitol accumulation in the tissues of the lens, and sciatic nerve for treated rats as compared to controls.

TABLE 2

| Test Compound | Dosage mg/kg/day | L | N |
|---|---|---|---|
| 2-thioxo-benz[cd]indole-1(2H)-acetic acid, ethyl ester | 150 | 11 | 36 |
| 2-thioxo-benz[cd]indole-1(2H)-acetic acid | 165 | 18 | 30 |
| 6-bromo-2-thioxo-benz[cd]indole-1(2H)-acetic acid | 131 | 27 | 80 |
| 6-chloro-2-thioxo-benz[cd]indole-1(2H)-acetic acid | 134 | 27 | 79 |
| 6-fluoro-2-thioxo-benz[cd]indole-1(2H)-acetic acid | 144 | | 49 |
| 6-iodo-2-thioxo-benz[cd]indole-1(2H)-acetic acid | 141 | 32 | 74 |
| 6,8-dibromo-2-thioxo-benz[cd]indole-1(2H)-acetic acid | 131 | 9 | |
| 6,8-dichloro-2-thioxo-benz[cd]indole-1(2H)-acetic acid | 128 | 18 | 25 |
| 2-thioxo-benz[cd]indole-1(2H)-acetic acid, 2-amino-ethyl ester, 4-methylphenylsulfonic acid salt | 162 | | 40 |
| 6-chloro-benz[cd]indole-1(2H)-acetic acid, 3-dimethylamino-1-propyl ester, hydrochloride | 144 | 28 | 57 |

PROCESS

The following reaction scheme illustrates a method of preparing the compounds of formula I.

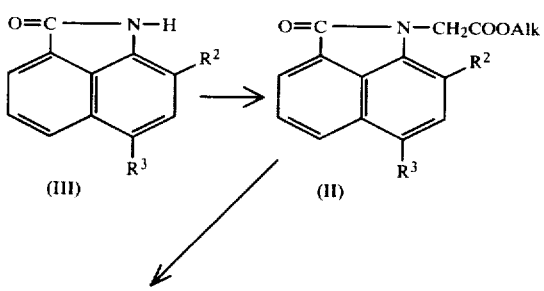

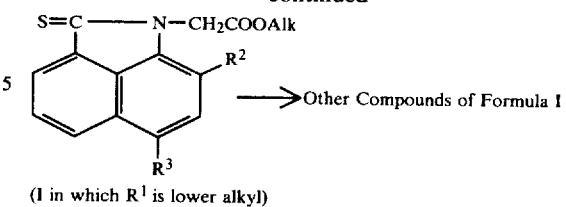

(I in which $R^1$ is lower alkyl)

The desired starting materials of formula III are either described or can be prepared by known halogenation methods of the compound of formula III, in which $R^2$ and $R^3$ are hydrogen. For example, see the reports by H. Goldstein and P. Francey, Helv., 15, 1366 (1932); Y. I. Rozhinskii, Zhur. Org. Khim., 8, 2388 (1972); A. P. Karishin and D. M. Kustol, Zhur. Obschch. Khim., 31, 1655 (1961); and Chemical Abstracts, 82, 97936p (1975) for U.S.S.R. Pat. No. 445,646, Oct. 5, 1974.

Alkylation of a compound of formula III gives the corresponding compound of formula II in which Alk, $R^2$ and $R^3$ are as defined herein. In a preferred method of alkylation, the compound of formula III is reacted with about a molar equivalent of a strong proton acceptor, preferably sodium hydride, in an inert organic solvent, preferably dimethylformamide, to obtain a solution containing the anion of the compound of formula III. To this solution, about one molar equivalent of a lower alkyl ester of bromo- or chloroacetic acid is added. The resulting solution is maintained at 100° to 150° C. for one to ten hours and the compound of formula II is isolated.

If desired, a compound of formula II can be converted to other compounds of formula II. For example, chlorination of a compound of formula II in which $R^2$ and $R^3$ are hydrogen with sulfuryl chloride gives the corresponding compound of formula II in which $R^2$ is hydrogen and $R^3$ is chloro.

Reaction of a compound of formula II with phosphorus pentasulfide affords the corresponding compound of formula I in which $R^1$ is lower alkyl and $R^2$ and $R^3$ are as defined herein. Preferably about 1.0 to 1.5 molar equivalents of phosphorus pentasulfide is used and pyridine is employed as a solvent. The reaction mixture is maintained at 90° to 115° C. for two to five hours and the ester of the compound of formula I is isolated.

If desired, the compound of formula I in which $R^1$ is lower alkyl can be converted to other compounds of formula I.

In one conversion, the compound of formula I in which $R^1$ is lower alkyl is hydrolyzed under alkaline conditions to obtain the correponding compound of formula I in which $R^1$ is hydrogen and $R^2$ and $R^3$ are as defined herein. Preferred conditions for the alkaline hydrolysis involves reacting the ester of formula I with about 1.1 to 1.8 molar equivalents of sodium hydroxide or potassium hydroxide in an aqueous solution of a lower alkanol, preferably methanol, at about 20° to 40° C. for one to five days. Acidification of the reaction mixture allows for the isolation of the compound of formula I in which $R^1$ is hydrogen.

Reaction of the ester of formula I in which $R^1$ is lower alkyl with a compound of the formula $HO—(CH_2)_m—NR^4R^5$ in which m, $R^4$ and $R^5$ are as defined herein affords the corresponding compound of formula I in which $R^1$ is $—(CH_2)_m—NR^4R^5$ wherein m, $R^4$ and $R^5$ are as defined herein and $R^2$ and $R^3$ are as defined herein. This reaction is conducted preferably at about 80° to 140° C. for about 5 to 15 hours, the lower alkanol so formed during the reaction being removed by evaporation from the reaction mixture. Although a reaction solvent is not a necessity, the reaction can be done in an inert organic solvent having a higher boiling point than the so formed lower alkanol.

Another method of preparing the compounds of formula I in which $R^1$ is —$(CH_2)_m$—$NR^4R^5$ wherein m, $R^4$ and $R^5$ are as defined herein and $R^2$ and $R^3$ are as defined herein involves the condensation of the compound of formula I in which $R^1$ is hydrogen with the compound of the formula HO—$(CH_2)_m$—$NR^4R^5$ wherein m, $R^4$ and $R^5$ are as defined herein. For this condensation, the compound of formula I in which $R^1$ is hydrogen is reacted preferably with about two molar equivalents of the compound of the formula HO—$(CH_2)_m$—$NR^4R^5$ in the presence of about two to three molar equivalents of p-toluenesulfonic acid hydrate in an inert organic solvent, preferably benzene, at about 70° to 100° C. for about one to four days and removing the formed water, for example in the form of an azeotrope of water and benzene.

If desired, the acid of formula I in which $R^1$ is hydrogen can be halogenated to obtain a halogenated acid of formula I in which $R^1$ is hydrogen and $R^2$ and/or $R^3$ is halo. For example, bromination of the compound of formula I in which $R^1$, $R^2$ and $R^3$ are hydrogen with about 1.0 to 1.5 molar equivalents of bromine in a solvent of glacial acetic acid at about 20° to 40° C. for about one to five hours affords the compound of formula I in which $R^1$ and $R^2$ are hydrogen and $R^3$ is bromo.

The following examples illustrate further this invention.

EXAMPLE 1

6,8-Dibromo-benz[cd]indol-2(1H)-one (III: $R^2$ and $R^3$=Br)

A solution of bromine (3.8 g) in glacial acetic acid (15 mL) was added dropwise to a suspension of 6-bromo-benz[cd]indol-2(1H)-one[4 g, 16.1 mmol, described by H. Goldstein and P. Francey, Helv., 15, 1366 (1932)] in glacial acetic acid (30 mL) for 3–4 hr. The precipitate was collected by filtration, washed, dried (any coloration caused by the excess of bromine could be removed by washing with a diluted sodium thiosulfate solution), and crystallized from ethanol-water to give the title compound (3.5 g): mp 280°–290° C.; Anal. Calcd for $C_{11}H_5Br_2NO$: C, 40.41% H, 1.54% N, 4.28% and Found: C, 40.52% H, 1.51% N, 4.43%; IR (mineral oil) 3140 and 1700 cm$^{-1}$; UV max (methanol) 345 ($\epsilon$4370), 329 (2910), 264 (27,680), and 212 nm (30,920); and NMR (DMSO-d$_6$)$\delta$ 8.0 (m, 4H), and 11.3 (s, 1H).

EXAMPLE 2

6,8-Dichloro-benz[cd]indol-2(1H)-one (III: $R^2$ and $R^3$=Cl)

Sulfuryl chloride (36.8 g, 22.1 mL, 0.273 mol) was added dropwise to a suspension of benz[cd]indol-2(1H)-one [20 g, 0.119 mol, described by E. E. Pisovschi, Bull. Soc. Chim., 9, 86 (1911)] in glacial acetic acid (275 mL) at room temperature with mechanical stirring. The mixture was heated to 60°–70° C. for 1.5 hr., and cooled to 20° C. The precipitate was collected by filtration, washed with glacial acetic acid, and crystallized from toluene (about 1500 mL) to give the title compound (24.2 g): mp 265° C.; Anal. Calcd for $C_{11}H_5Cl_2NO$: C, 55.50% H, 2.12% N, 5.88%; and Found: C, 55.29% H, 2.04% N, 5.89%; IR (mineral oil) 3170, 1720, and 1700 cm$^{-1}$; UV max (methanol) 257 nm ($\epsilon$27,900); and NMR (DMSO-d$_6$)$\delta$ 7.55 (s, 1H), 8.05 (m, 3H), and 11.25 (s, 1H). The title compound is described by Y. I. Rozhinskii, Zhur. Org. Khim., 8, 2388, (1972).

EXAMPLE 3

6-Bromo-2-oxo-benz[cd]indol-1(2H)-acetic Acid, Ethyl Ester (II: Alk=ethyl, $R^2$=H and $R^3$=Br)

Sodium hydride (0.63 g, 0.0262 mol; 1.26 g of a 50% mineral oil suspension) was added portionwise with stirring to a solution of 6-bromo-benz[cd]indol-2(1H)-one (6.5 g, 0.0262 mol) in dry dimethylformamide (20 mL) allowing hydrogen evolution to cease before adding the next portion of hydride. To the cooled (ice-bath), stirred solution was added ethyl chloroacetate (3.53 g, 3.17 mL, 0.0288 mol) and the mixture was refluxed for 3 hr. The solvent was evaporated in vacuo and the residue was triturated with water (the mixture was stirred overnight at room temperature). The precipitate was separated by filtration, washed with water and hexane (10 mL; to remove mineral oil), dried (8.4 g) and crystallized from ethanol to give the title compound (5.8 in two crops): mp 128°–130° C.; Anal. Calcd for $C_{15}H_{12}BrNO_3$: C, 53.91% H, 3.62% N, 4.19%; Found: C, 53.58% H, 3.75% N, 4.26%; IR (CHCl$_3$) 1744, 1708, 1629, 1602, and 1194 cm$^{-1}$; UV max (methanol) 339 ($\epsilon$5600), 323 (2800), 289 (sH, 4650), 279 (6200), and 258 nm (18,600);, and NMR (CDCl$_3$)$\delta$ 1.25 (t, 3H), 4.20 (q, 2H), 4.62 (s, 2H), 6.63 (d, 1H), 7.60 (d, 1H), 7.77 (d, 1H), 8.07 (m, 2H).

In the same manner, but replacing 6-bromo-benz[cd]indol-2(1H)-one with an equivalent amount of 6-fluoro-benz[cd]indol-2(1H)-one [described by A. P. Korishin and D. M. Kustol, Zhur. Obschch. Khim., 31, 1655 (1961)]; 6-iodo-benz[cd]indol-2(1H)-one (described by A. P. Karishin and D. M. Kustol, cited above); 6,8-dibromo-benz[cd]indol-2(1H)-one (described in Example 1); 6,8-dichloro-benz[cd]indol-2(1H)-one (described in Example 2) or benz[cd]indol-2(1H)-one, the following compounds of formula II are obtained respectively: 6-fluoro-2-oxo-benz[cd]indole-1(2H)-acetic acid, ethyl ester: mp 105°–106° C. (crystallized from ethanol): Anal. Calcd for $C_{15}H_{12}FNO_3$: C, 65.93% H, 4.43% N, 5.13% and Found: C, 66.21% H, 4.59% N, 5.03%; IR (CHCl$_3$) 1745 and 1705 cm$^{-1}$; UV max (methanol) 336 ($\epsilon$2795), 320 (2140), 275 (7125), 256 (18,390), 254 (18,340), and 214 nm (38,175); NMR (CDCl$_3$)$\delta$ 1.25 (t, 3H), 4.2 (q, 2H), 4.65 (s, 2H), 6.9 (m, 5H); 6-iodo-2-oxo-benz[cd]indole-1(2H)-acetic acid, ethyl ester: mp 145°–147° C. (crystallized from ethanol-water); Anal. Calcd for $C_{15}H_{12}INO_3$: C, 47.29% H, 3.17% N, 3.67% and Found: C, 48.58% H, 3.64% N, 3.43%; IR (CHCl$_3$) 1750 and 1707 cm$^{-1}$; UV max (methanol) 340 ($\epsilon$3960), 324 (2665), 310 (1525), 280 (5840), and 257 nm (16,555); NMR (CDCl$_3$)$\delta$ 1.25 (t, 3H), 4.2 (q, 2H), 4.6 (s, 2H), 6.6 (d, 1H), and 7.9 (m, 4H); 6,8-dibromo-2-oxo-benz[cd]indole-1(2H)-acetic acid, ethyl ester: mp 152°–153° C. (crystallized from ethanol); Anal. Calcd for $C_{15}H_{11}Br_2NO_3$: C, 43.62% H, 2.68% N, 3.39% and Found: C, 43.47% H, 2.68% N, 3.38%; IR (CHCl$_3$) 1710 and 1740 cm$^{-1}$; UV max (methanol) 346 ($\epsilon$3980), 329 (2735), 290 (4410), 263 (13,325), 220 (29,690), and 215 nm (28,370); NMR (CDCl$_3$)$\delta$ 1.28 (t, 3H), 4.23 (q, 2H), 4.95 (s, 2H), 7.95 (m, 4H); 6,8- dichloro-2-oxo-benz[cd]indole-1(2H)-acetic acid, ethyl ester: mp 125°–126° C. (crystallized from ethanol-water); Anal. Calcd for $C_{15}H_{11}Cl_2NO_3$: C, 55.58% H, 3.42% N, 4.32% and Found: C, 55.62% H, 3.42% N, 4.34%; IR (CHCl$_3$) 1710 and 1745 cm$^{-1}$; UV max (methanol) 345 ($\epsilon$3980), 328 (2740), 260 (23,400), and 220 nm (30,550); NMR (CDCl$_3$)δ 1.26 (t, 3H), 4.22 (q, 2H), 4.93 (s, 2H), 7.36 (s, 1H), 7.76 (t, 1H), and 8.15 (d, 2H); and 2-oxo-benz[cd]indole-1(2H)-acetic acid, ethyl ester: mp 86°–87° C. (crystallized from isopropanol-water); IR (CHCL$_3$) 1750 and 1705 cm$^{-1}$; and NMR (CDCl$_3$)δ 1.25 (t, 3H), 4.21 (q, 2H), 4.65 (s, 2H), 6.75 (2d, 1H) and 7.15–8.25 (m, 5H).

EXAMPLE 4

6-Chloro-2-oxo-benz[cd]indole-1-(2H)-acetic Acid, Ethyl Ester (II: Alk=ethyl, $R^2$=H and $R^3$=Cl)

To a suspension of 2-oxo-benz[cd]indole-1(2H)acetic acid, ethyl ester (17 g, 0.067 mole, described in Example 3) in glacial acetic acid (67 mL) was added sulfuryl chloride (9 g, 5.4 ml, 0.067 mol) dropwise at room temperature over a period of 50 min with mechanical stirring. The solid initially disappeared after a few milliliters of the chloride were added. Towards the end of additon, the product started to precipitate. The reaction mixture was stirred at room temperature for an additional 30 min and then at 94° C. for 2 hr. After cooling to room temperature the mixture was poured into water (200 mL). The precipitate was filtered, dried (18.3 g), and crystallized from boiling ethanol (360 mL) to give the title compound: mp 138°–140° C.; Anal. Calcd for $C_{15}H_{12}ClNO_3$: C, 62.19% H, 4.18% N, 4.83% and Found: C, 61.98% H, 4.08% N, 4.82%; IR (CHCl$_3$) 1745 and 1710 cm$^{-1}$; UV max (methanol) 339 ($\epsilon$3690), 322 (2530), 279 (6030), 258 (18,680) and 214 nm (32,760); NMR (CDCl$_3$)δ 1.25 (t, 3H), 4.2 (q, 2H), 4.65 (s, 2H), and 7.5 (m, 5H).

EXAMPLE 5

6-Bromo-2-thioxo-benz[cd]indole-1(2H)-acetic Acid, Ethyl Ester (I: $R^1$=ethyl, $R^2$=H and $R^3$=Br)

A solution of 6-bromo-2-oxo-benz[cd]indole-1(2H)-acetic acid, ethyl ester (4.0 g, 12 mmol, described in Example 3), pyridine (18 mL) and phosphorus pentasulfide (3.2 g, 14.4 mmol) was refluxed for 2–3 hr (until reaction was complete). The mixture was poured into hot water (150 mL) and the suspension was stirred for 1.5 hr at room temperature. The solid material was collected by filtration, washed with water, dried and crystallized from ethanol to give the title compound (2.65 g): mp 163°–164° C., Anal. Calcd for $C_{15}H_{12}BrNO_2S$: C, 51.44% H, 3.45% N, 4.00% and Found: C, 51.31% H, 3.50% N, 4.01%; IR (CHCl$_3$)1744, 1628, 1592, and 1191 cm$^{-1}$; UV max (methanol) 359 ($\epsilon$4640), 343 (3030), 311 (8140), 300 (7860), 273 (27,700, and 264 nm (20,090); NMR (CDCl$_3$)δ 1.25 (t, 3H), 4.21 (g, 2H), 5.02 (s, 2H), 6.75 (d, 1H), 7.60 (d, 1H), and 8.00 (m, 3H).

In the same manner, but replacing 6-bromo-2-oxo-benz[cd]indole-1(2H)-acetic acid, ethyl ester with an equivalent amount of another compound of formula II described in Examples 3 and 4, the following compounds of formula I were obtained respectively: 6-fluoro-2-thioxo-benz[cd]indole-1(2H)-acetic acid, ethyl ester: mp 134°–135° C. (crystallized from ethanol-water); Anal. Calcd for $C_{15}H_{12}FNO_2S$: C, 62.27% H, 4.18% N, 4.84% and Found: C, 62.15% H, 4.18% N, 4.74%; IR (CDCl$_3$) 1745 cm$^{-1}$; UV max (methanol) 339 ($\epsilon$2570), 309 (8275), 296 (8500), 270 (28,390) and 262 nm (21,400); NMR (CDCl$_3$)δ 1.25 (t, 3H), 4.2 (q, 2H), 5.05 (s, 2H), and 7.5 (m, 5H); 6-iodo-2-thioxo-benz[cd]indole-1(2H)-acetic acid, ethyl ester: mp 178°–179° C. (crystallized from ethanol); Anal. Calcd for $C_{15}H_{12}INO_2S$: C, 45.36% H, 3.05% N, 3.53% and Found: C, 45.11% H, 2.93% H, 3.53%; IR (CHCl$_3$) 1745 cm$^{-1}$; UV max (methanol) 346 ($\epsilon$2510), 315 (6715), 3030 (6380) 275 (17,860), 226 (19,135), and 213 nm (20,140); NMR (CDCl$_3$)δ 1.25 (t, 3H), 4.25 (q, 2H), 5.05 (s, 2H), 6.7 (d, 1H), and 7.9 (m, 4H); 6,8-dibromo-2-thioxo-benz[cd]indole-1(2H)-acetic acid, ethyl ester: mp 154°–156° C. (crystallized from ethanol); Anal. Calcd for $C_{15}H_{11}Br_2NO_2S$: C, 41.98% H, 2.58% N, 3.26% and Found: C, 41.98% H, 2.62% N, 3.27%; IR (CHCl$_3$) 1740 and 1460 cm$^{-1}$; UV max (methanol) 346 ($\epsilon$2595), 302 (7320), 301 (7395), 275 (35,030), and 267 nm (23,355); NMR (CDCl$_3$)δ]1.25 (t, 3H), 4.2 (q, 2H), 5.45 (s, 2H), and 8.00 (m, 4H); 6,8-dichloro-2-thioxo-benz[cd]indole-1(2H)-acetic acid, ethyl ester: mp 126°–127° C. (crystallized from ethanol); Anal. Calcd for $C_{15}H_{11}Cl_2NO_2S$: C, 52.96% H, 3.26% N, 4.12% and Found: C, 52.71% H, 3.33% N, 4.21%; IR (CHCl$_3$) 1745 cm$^{-1}$; UV max (methanol) 348 ($\epsilon$2380), 314 (7360), 303 (7280), 275 (35,440), and 267 nm (22,700); NMR (CDCl$_3$)δ 1.25 (t, 3H), 4.2 (q, 2H), 5.45 (s, 2H), 7.7 (m, 4H); 2-thioxo-benz[cd]indole-1(2H)-acetic acid, ethyl ester: mp 143°–144° C. (crystallized from ethanol; Anal. Calcd for $C_{15}H_{13}NO_2S$: C, 66.40% H, 4.83% N, 5.16% and Found: C, 66.05% H, 4.92% N, 5.18%; IR (CHCl$_3$) 1745 and 1370 cm$^{-1}$; UV max (methanol) 342 ($\epsilon$3600), 309 (7200), 303 (7300), 267 (29,900), and 259 nm (23,250); NMR (CDCl$_3$)δ 1.25 (t, 3H), 4.2 (q, 2H), 5.05 (s, 2H), 7.6 (m, 6H); and 6-chloro-2-thioxo-benz[cd]indole-1(2H)-acetic acid, ethyl ester: mp 148°–149° C. (crystallized from ethanol); Anal. Calcd for $C_{15}H_{12}ClNO_2S$: C, 58.92% H, 3.96% N, 4.58% and Found: C, 58.38% H, 3.96% N, 4.64% IR (CHCl$_3$) 1745 cm$^{-1}$; UV max (methanol) 342 ($\epsilon$3200), 310 (8200), 272 (28,100) and 254 nm (20,700); NMR (CDCl$_3$)δ 1.27 (t, 3H), 4.20 (q, 2H), 5.05 (s, 2H), 6.80 and 7.41 (2d, 2H), 7.73 (2d, 1H) and 8.20 (2d, 2H).

EXAMPLE 6

6-Bromo-2-thioxo-benz[cd]indole-1(2H)-acetic Acid (I: $R^1$ and $R^2$=H and $R^3$=Br)

A suspension of 6-bromo-2-thioxo-benz[cd]indole-1(2H)-acetic acid, ethyl ester (2.5 g, 7.1 mmol, described in Example 5) in methanol (70 mL) and 2 N aqueous sodium hydroxide (5.3 mL) was stirred at room temperature for 2 days and evaporated. The residue was dissolved in water (300 mL, with slight warming), and the solution was acidified. The precipitate was collected by filtration, dried, and crystallized from ethanol-water to give the title compound (2.05 g): mp 253° C. (245° C. darkening); Anal. Calcd for $C_{13}H_8BrNO_2S$: C, 48.46% H, 2.50% N, 4.35% and Found: C, 48.32% H, 2.62% N, 4.38%; IR (mineral oil) 3100, and 1715 cm$^{-1}$; UV max (methanol) 436 ($\epsilon$12,830), 361 (4680), 342 (3130), 311 (8140), 302 (sh, 7950), and 273 nm (24,160); NMR (DMSO-d$_6$)δ 5.08 (s, 2H), 7.30 (d, 1H), 7.90 (d, 1H), and 8.00 (m, 3H).

In the same manner, but replacing 6-bromo-2-thioxo-benz[cd]indole-1(2H)-acetic acid, ethyl ester with another ester of formula I described in Example 5, the following acids of formula I were obtained, respectively: 6-fluoro-2-thioxo-benz[cd]indole-1(2H)-acetic acid; mp 244° C. (crystallized from ethanol-water); Anal. Calcd for C$_{13}$H$_8$FNO$_2$S: C, 59.76% H, 3.09% N, 5.36% and Found: C, 60.54% H, 3.56% N, 5.42%; IR (mineral oil) 2900, 1728 cm$^{-1}$; UV max (methanol) 357 (ε3265), 349 (1640), 339 (2460), 306 (8355), 297 (8580), 270 (27,230) and 263 nm (20,890); NMR (DMSO-d$_6$)δ 5.1 (s, 2H), 7.8 (m, 4H), and 10.3 (broad); 6-iodo-2-thioxo-benz[cd]indole-1(2H)-acetic acid: mp 245°–247° C. (crystallized from ethanol); Anal. Calcd For C$_{13}$H$_8$INO$_2$S: C, 42.29% H, 2.18% N, 3.79% and Found: C, 42.23% H, 2.24% N, 3.84%; IR (mineral oil) 2950 and 1717 cm$^{-1}$; UV max (methanol) 343 (ε3280), 273 (21,440), 223 (24,150), and 210 nm (25,260); NMR (DMSO-d$_6$)δ 5.1 (s, 2H), and 7.7 (m, 5H); 6,8-dibromo-2-thioxo-benz[cd]indole-1(2H)-acetic acid: mp 253°–255° C. (crystalized from ethanol); Anal. Calcd for C$_{13}$H$_7$Br$_2$NO$_2$S: C, 38.93% H, 1.76% N, 3.49% and Found: C, 39.38% H, 1.84% N, 3.53%; IR (mineral oil) 2900 (broad), and 1720 cm$^{-1}$; UV max (methanol), 349 (ε2735), 316 (7070), 304 (7030), 278 (27,937), and 217 nm (26,220); NMR (DMSO-d$_6$)δ 5.35 (s, 2H), 8.0 (m, 4H), and 13.0 (broad, 1H); 6,8-dichloro-2-thioxo-benz[cd]indole-1(2H)-acetic acid: mp 262°–264° C. (crystallized from ethanol); Anal. Calcd for C$_{13}$H$_7$Cl$_2$NO$_2$S: C, 50.02% H, 2.26% N, 4.49% and Found: C, 50.11% H, 2.26% N, 4.62%; IR (mineral oil) 2900 (broad), and 1723 cm$^{-1}$; UV max (methanol 348 (ε2600), 313 (7300), 304 (7170), 275 (30,930), and 213 nm (25,990); NMR (DMSO-d$_6$)δ 5.25 (s, 2H), 7.9 (m, 4H), and 13.2 (broad, 1H); 2-thioxo-benz[cd]indole-1(2H)-acetic acid: mp 230°–232° C. (crystallized from ethanol-water); Anal. Calcd for C$_{13}$H$_9$NO$_2$S: C, 64.18% H, 3.73% N, 5.76% and Found: C, 64.26% H, 3.73% N, 5.72%; IR (mineral oil) 3000 (broad), and 1720 cm$^{-1}$; UV max (methanol) 359 (ε6100), 342 (3700), 310 (7300), 304 (7400), 267 (27,750), and 263 nm (sh, 22,700); NMR (DMSO-d$_6$)δ 5.15 1 (s, 2H), and 7.9 (m, 6H); and 6-chloro-2-thioxo-benz[cd]indole-1(2H)-acetic acid: mp 255°–258° C. (crystallized from acetic acid); Anal. Calcd for C$_{13}$H$_8$ClNO$_2$S: C, 56.22% H, 2.90% N, 5.04% and Found: C, 55.97% H, 2.89% N, 5.14%; IR (mineral oil) 2900 (broad), and 1720 cm$^{-1}$; UV max (methanol) 342 (ε3080), 310 (8010), 300 (7840), and 272 nm (26,170); NMR (DMSO-d$_6$)δ 5.1 (s, 2H), and 7.8 (m, 5H).

EXAMPLE 7

Alternative Preparation of 6-bromo-2-thioxo-benz[cd]indole-1(2H)-acetic Acid

To a suspension of 2-thioxo-benz[cd]indole-1(2H)-acetic acid (4.2 g, 17.26 mmol, described in Example 6), in glacial acetic acid (80 mL) was added a solution of bromine (3.59 g, 22.44 mmol) in glacial acetic acid (20 mL) in two portions with mechanical stirring within one hour. After initial clearing of the suspension, a heavy precipitate was formed. More acetic acid (60 mL) was added in order to make stirring more efficient. The mixture was filtered and the precipitate was washed twice with water (150 mL), dried, crystallized from ethanol-water giving 4.7 g in two crops and recrystallized from methanol to give 3.0 g of the title compound, identical in all respects to that prepared in Example 6.

EXAMPLE 8

2-Thioxo-benz[cd]indole-1(2H)-acetic Acid, 2-Amino-ethyl Ester (I: R$^1$=2-amino-ethyl and R$^2$ and R$^3$=H)

A suspension of 2-thioxo-benz[cd]indole-1(2H)-acetic acid (1.0 g, 4.11 mmol, described in Example 6) aminoethanol (0.5 g, 0.49 mL, 8.22 mmol) and p-toluenesulfonic acid hydrate (1.88 g, 9.86 mmol) in benzene (50 mL) was refluxed for 48 hr with stirring in a Soxhlet apparatus containing a thimble filled with 3A molecular sieves. The mixture was evaporated to dryness, and the residue was triturated with cold water (50 mL). The precipitate was collected by filtration, washed with diethyl ether (50 mL), and crystallized from water to give the 4-methylphenylsulfonic acid salt of the title compound (1.0 g): Anal. Calcd for C$_{15}$H$_{14}$N$_2$O$_2$S.C$_7$H$_8$O$_3$S: C, 57.63% H, 4.84% N, 6.11% and Found: C, 57.58% H, 4.94% N, 6.23%; IR (mineral oil) 2900, 1740, 1375, and 11700 cm$^{-1}$; UV max (methanol) 342 (ε3400), 310 (6700), 304 (6740), 267 (27,900), 259 (21,580), and 218 nm (26,210); NMR (DMSO-d$_6$)ε 2.25 (s, 3H), 3.12 (t, 2H), 4.32 (t, 2H), 5.3 (s, 2H), 7.7 (m, 10H), and 7.9 (s, 3H).

EXAMPLE 9

6-Chloro-2-thioxo-benz[cd]indole-1(2H)-acetic Acid, 3-Dimethylamino-1propyl Ester (I:R$^1$=3-dimethylaminopropyl and R$^2$ and R$^3$=H)

A solution of 6-chloro-2-thioxo-benz[cd]indole-1(2H)-acetic acid, ethyl ester (5.0 g, 16.4 mmol, described in Example 5) and 3-dimethylaminopropanol (25 mL) were heated with stirring at 100°–120° C. for 6 hr during which time a slow continuous stream of nitrogen gas was blown over the surface of the mixture. At the end, the temperature was increased to 140° C. for 1 hr. The excess of the amino alcohol was removed in high vacuum, and the residue triturated with water. The mixture was extracted with ethyl acetate (3×100 mL), and the organic extracts washed with sodium bicarbonate solution, and brine. The organic phase was extracted with 0.5 N aqueous hydrochloric acid (4×50 mL) and the aqueous extract was evaporated to dryness. The residue was crystallized from ethanol-diethyl ether to give the hydrochloride salt of the title compound (3.7 g): mp 175°–176° C.; Anal. Calcd for C$_{18}$H$_{19}$ClN$_2$O$_2$S.HCl: C, 54.14% H, 5.05% N, 7.01% Found: C, 54.01% H, 5.06% N, 6.97%; IR (mineral oil) 2600, and 1750 cm$^{-1}$; UV max (methanol ) 342 (ε3900), 310 (8300), 303 (8200), 272 (29,100), and 264 nm (21,300); NMR (DMSO-d$_6$)δ 2.0 (m, 2H), 2.7 (s, 6H), 3.05 (m, 2H), 4.2 (5, 2H), 5.25 (s, 2H), 7.4 (m, 5H), and 11.0 (broad, 1H).

I claim:
1. A compound of the formula

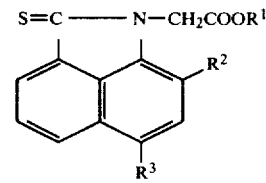

in which R$^1$ is hydrogen, lower alkyl, or —(CH$_2$)$_m$—NR$^4$R$^5$ wherein m is an integer from 2 to 6 and R$^4$ and R[5] each is hydrogen or lower alkyl; R[2] is hydrogen, bromo or chloro; and r[3] is hydrogen or halo; with the proviso that when R[2] is bromo or chloro, then R[3] is bromo or chloro, or a therapeutically acceptable salt thereof.

2. A compound of claim 1 wherein R[1] is hydrogen, lower alkyl, or —(CH$_2$)$_m$—NR[4]R[5] wherein m is 2 or 3 and R[4] and R[5] each is hydrogen, methyl or ethyl; R[2] is hydrogen and R[3] is hydrogen or halo; or R[2] and R[3] are the same and are selected from bromo and chloro; or a therapeutically acceptable salt thereof.

3. A compound of claim 1 wherein R[1] and R[2] are hydrogen, and R[3] is hydrogen or halo; or a therapeutically acceptable base addition salt thereof.

4. 2-Thioxo-benz[cd]indole-1(2H)-acetic acid, ethyl ester, as claimed in claim 1.

5. 6-Chloro-2-thioxo-benz[cd]indole-1(2H)-acetic acid, ethyl ester, as claimed in claim 1.

6. 6-Bromo-2-thioxo-benz[cd]indole-1(2H)-acetic acid, as claimed in claim 1.

7. 6-Fluoro-2-thioxo-benz[cd]indole-1(2H)-acetic acid, as claimed in claim 1.

8. 6-Iodo-2-thioxo-benz[cd]-indole-1(2H)-acetic acid, as claimed in claim 1.

9. 6,8-Dibromo-2-thioxo-benz[cd]indole-1(2H)-acetic acid, as claimed in claim 1.

10. 6,8 -Dichloro-2-thioxo-benz[cd]indole-1(2H)-acetic acid, as claimed in claim 1.

11. 6-Chloro-2-thioxo-benz[cd]indole-1(2H)-acetic acid, as claimed in claim 1.

12. 2-Thioxo-benz[cd]indole-1(2H)-acetic acid, as claimed in claim 1.

13. 2-Thioxo-benz[cd]indole-1(2H)-acetic acid, 2-amino-ethyl ester, as claimed in claim 1.

14. 6-Chloro-2-thioxo-benz[cd]indole-1(2H)-acetic acid, 3-dimethyl-amino-1-propyl ester, as claimed in claim 1.

15. A pharmaceutical composition, for preventing or relieving diabetic complications, consisting of neuopathy, nephropathy, retinopathy, and cataracts, in a diabetic mammal, which comprises an effective amount of a compound of the formula

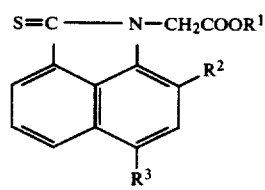

in which R[1] is hydrogen, lower alkyl, or —(CH$_2$)$_m$-NR[4]R[5] wherein m is an integer from 2 to 6 and R[4] and R[5] each is hydrogen or lower alkyl; R[2] is hydrogen, bromo or chloro; and R[3] is hydrogen or halo; with the proviso that when R[2] is bromo or chloro, then R[3] is bromo or chloro, or a therapeutically acceptable salt thereof, and a pharmaceutically acceptable carrier.

16. A method of preventing or relieving diabetic complications, consisting of neuropathy, nephropathy, retinopathy, and cataracts, in a diabetic mammal, which comprises administering to said mammal an alleviating or prophylactic amount of a composition of claim 15, or a therapeutically acceptable salt thereof.

17. A compound of claim 1 wherein R[1] is hydrogen and R[2] and R[3] are the same and are selected from bromo and chloro.

* * * * *